United States Patent
Sato

(10) Patent No.: US 9,867,559 B2
(45) Date of Patent: Jan. 16, 2018

(54) MEASUREMENT DEVICE, MEASUREMENT METHOD, PROGRAM AND RECORDING MEDIUM

(71) Applicant: Sony Corporation, Tokyo (JP)

(72) Inventor: Hideo Sato, Tokyo (JP)

(73) Assignee: Sony Corporation (JP)

( * ) Notice: Subject to any disclaimer, the term of this patent is extended or adjusted under 35 U.S.C. 154(b) by 311 days.

(21) Appl. No.: 14/364,580

(22) PCT Filed: Nov. 22, 2012

(86) PCT No.: PCT/JP2012/080334
§ 371 (c)(1),
(2) Date: Jun. 11, 2014

(87) PCT Pub. No.: WO2013/094362
PCT Pub. Date: Jun. 27, 2013

(65) Prior Publication Data
US 2014/0350365 A1   Nov. 27, 2014

(30) Foreign Application Priority Data
Dec. 19, 2011 (JP) ................................. 2011-277613

(51) Int. Cl.
*A61B 5/1455* (2006.01)
*A61B 5/145* (2006.01)
(Continued)

(52) U.S. Cl.
CPC .......... *A61B 5/1455* (2013.01); *A61B 5/0084* (2013.01); *A61B 5/02427* (2013.01);
(Continued)

(58) Field of Classification Search
None
See application file for complete search history.

(56) References Cited

U.S. PATENT DOCUMENTS 5,009,230 A   4/1991   Hutchinson

FOREIGN PATENT DOCUMENTS

JP    61-83924 A      4/1986
JP    2004-113434 A   4/2004
(Continued)

OTHER PUBLICATIONS

International Search Report from International Publication PCT/JP2012/080334 dated Jan. 8, 2013.

*Primary Examiner* — Eric Winakur
*Assistant Examiner* — Marjan Fardanesh
(74) *Attorney, Agent, or Firm* — Lerner, David, Littenberg, Krumholz & Mentlik, LLP

(57) ABSTRACT

There is provided a measurement device including a measurement unit configured to have a light source unit configured to emit measurement light having at least one kind of wavelength for measuring a biological component included inside a living body, a detection unit configured to detect the measurement light emitted from the inside of the living body, and a polarization control unit configured to be provided in at least one position between the light source unit and the living body or between the living body and the detection unit and to control a polarization direction of the measurement light, and an analysis unit configured to compute an optical rotation degree based on a change in a polarization state of the measurement light using a measurement result obtained by the measurement unit and to analyze a concentration of the biological component based on the computed optical rotation degree.

14 Claims, 12 Drawing Sheets

(51) Int. Cl.
  *A61B 5/024* (2006.01)
  *A61B 5/00* (2006.01)
  *A61B 5/01* (2006.01)

(52) U.S. Cl.
  CPC ...... *A61B 5/14532* (2013.01); *A61B 5/14552* (2013.01); *A61B 5/14558* (2013.01); *A61B 5/01* (2013.01); *A61B 2560/0223* (2013.01)

(56) References Cited

FOREIGN PATENT DOCUMENTS

| | | |
|---|---|---|
| JP | 2005-106592 A | 4/2005 |
| JP | 2005-274380 A | 10/2005 |
| JP | 2009-273819 A | 11/2009 |
| JP | 4706028 B2 | 6/2011 |

FIG. 6
| COMBINATION OF POLARIZATION DIRECTIONS ON LIGHT SOURCE UNIT SIDE | COMBINATION OF POLARIZATION DIRECTIONS ON DETECTION UNIT SIDE |
|---|---|
| 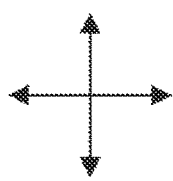 | 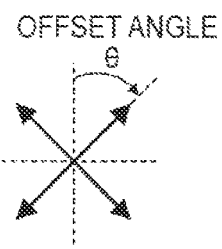 |
FIG. 7A
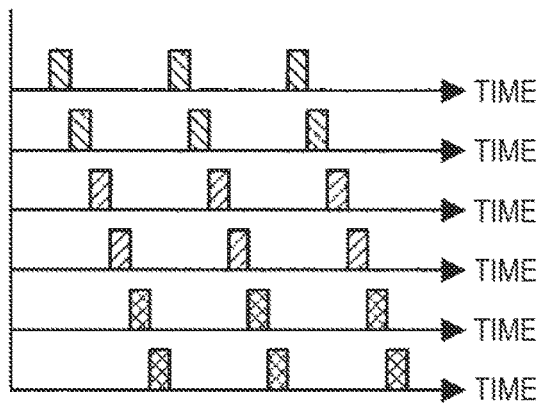
FIG. 7B
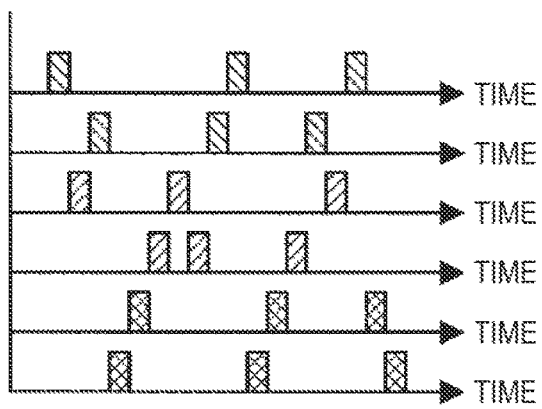

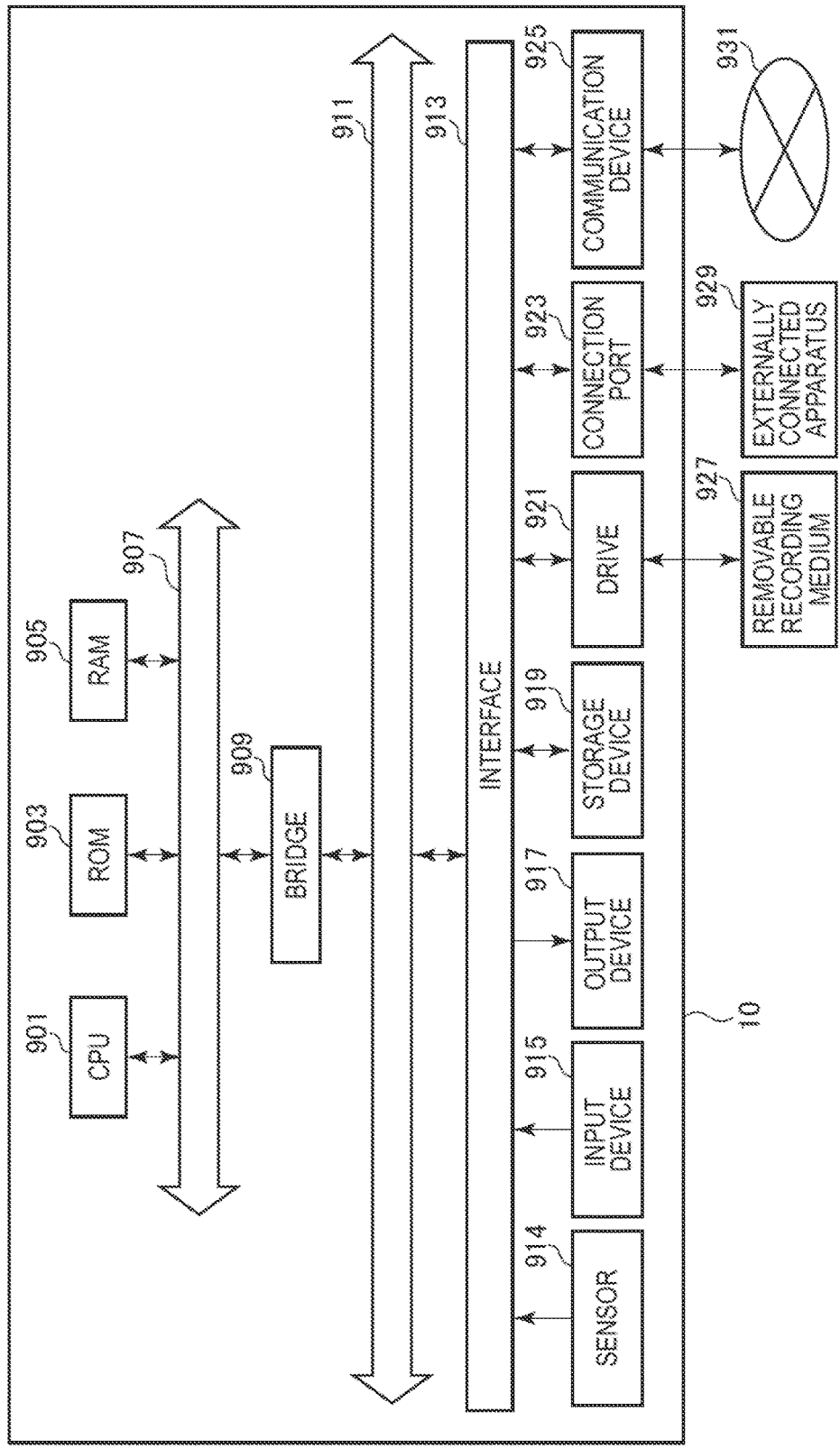

MEASUREMENT DEVICE, MEASUREMENT METHOD, PROGRAM AND RECORDING MEDIUM

CROSS-REFERENCE TO RELATED APPLICATION

The present application is a national phase entry under 35 U.S.C. §371 of International Application No. PCT/JP2012/080334 filed Nov. 22, 2012, published on Jun. 27, 2013 as WO 2013/094362 A1, which claims priority from Japanese Patent Application No. JP 2011-277613, filed in the Japanese Patent Office on Dec. 19, 2011.

TECHNICAL FIELD

The present disclosure relates to a measurement device, a measurement method, a program and a recording medium.

BACKGROUND ART

Researches relating to a technology of measuring a component in blood (biological component) included in an in vivo substance present under the skin or in the blood of a living body in a non-invasive manner have progressed. In a technology of analyzing a biological component in such a non-invasive optical scheme, a concentration of the biological component can be generally specified using light absorptance (for example, refer to Patent Literature 1 below).

CITATION LIST

Patent Literature

Patent Literature 1: JP 2009-273819A

SUMMARY OF INVENTION

Technical Problem

Here, in the biological component concentration measurement device shown in Patent Literature 1 described above, a concentration of a biological component is measured based on intensity of light that has been transmitted through a living body (transmitted light), but since the living body is a substance that easily scatters light and part of radiated light is absorbed by biological components included in the living body, there is a possibility of transmitted light not being sufficiently obtained depending on intensity of radiated light. Thus, in such a biological component concentration measurement device using such a non-invasive optical scheme as shown in Patent Literature 1 described above, it is preferable to use a light source that can emit light having sufficient intensity or a detector that can detect weak transmitted light, and accordingly such a device tends to have an increased size. In addition, when a concentration of glucose in blood is measured as a biological component, it is necessary to measure a scattering characteristic of transmitted light or a change caused by pulsebeats of the transmitted light, and accordingly, the device becomes larger. For this reason, miniaturization of a device while maintaining detection accuracy has been demanded.

Thus, the present disclosure considers the above circumstances and proposes a measurement device, a measurement method, a program, and a recording medium that can achieve further miniaturization of the device.

Solution to Problem

According to an aspect of the present disclosure, there is provided a measurement device including a measurement unit configured to have a light source unit configured to emit measurement light having at least one kind of wavelength for measuring a biological component included inside a living body, a detection unit configured to detect the measurement light emitted from the inside of the living body, and a polarization control unit configured to be provided in at least one position between the light source unit and the living body or between the living body and the detection unit and to control a polarization direction of the measurement light, and an analysis unit configured to compute an optical rotation degree based on a change in a polarization state of the measurement light using a measurement result obtained by the measurement unit and to analyze a concentration of the biological component based on the computed optical rotation degree.

According to an aspect of the present disclosure, there is provided a measurement method including emitting measurement light having at least one kind of wavelength for measuring a biological component included inside a living body, controlling a polarization direction of the measurement light in at least one position between a light source of the measurement light and the living body or between the living body and a detection unit configured to detect the measurement light emitted from the inside of the living body, detecting the measurement light emitted from the inside of the living body, and computing an optical rotation degree based on a change in a polarization state of the measurement light using a detection result of the measurement light and analyzing a concentration of the biological component based on the computed optical rotation degree.

According to an aspect of the present disclosure, there is provided a program causing a computer configured to be capable of communicating with a measuring instrument having a light source unit configured to emit measurement light having at least one kind of wavelength for measuring a biological component included inside a living body, a detection unit configured to detect the measurement light emitted from the inside of the living body, and a polarization control unit configured to be provided in at least one position between the light source unit and the living body or between the living body and the detection unit and to control a polarization direction of the measurement light to execute an analysis function of computing an optical rotation degree based on a change in a polarization state of the measurement light using a measurement result obtained by the measuring instrument and analyzing a concentration of the biological component based on the computed optical rotation degree.

According to an aspect of the present disclosure, there is provided a recording medium having a program recorded therein, the program causing a computer configured to be capable of communicating with a measuring instrument having a light source unit configured to emit measurement light having at least one kind of wavelength for measuring a biological component included inside a living body, a detection unit configured to detect the measurement light emitted from the inside of the living body, and a polarization control unit configured to be provided in at least one position between the light source unit and the living body or between the living body and the detection unit and to control a polarization direction of the measurement light to execute an analysis function of computing an optical rotation degree based on a change in a polarization state of the measurement light using a measurement result obtained by the measuring instrument and thereby analyzing a concentration of the biological component based on the computed optical rotation degree.

According to an aspect of the present disclosure, there is provided a measurement device including a measurement unit configured to have a light source unit configured to emit measurement light having at least one kind of wavelength for measuring a biological component included inside a living body, a detection unit configured to detect the measurement light emitted from the inside of the living body, and a polarization control unit configured to be provided in at least one position between the light source unit and the living body or between the living body and the detection unit and to control a polarization direction of the measurement light, an analysis unit configured to compute an optical rotation degree based on a change in a polarization state of the measurement light using a measurement result obtained by the measurement unit and to analyze a concentration of the biological component based on the computed optical rotation degree, and a measurement control unit configured to control the measurement unit. The measurement unit is a measurement section configured to detect the measurement light emitted from the living body as a result of scattering of the measurement light inside the living body and then reflection of the measurement light inside the living body. The measurement control unit switches polarization directions of the measurement light in a time division manner.

According to an aspect of the present disclosure, there is provided a measurement method including emitting measurement light having at least one kind of wavelength for measuring a biological component included inside a living body, controlling a polarization direction of the measurement light in at least one position between a light source of the measurement light and the living body or between the living body and a detection unit configured to detect the measurement light emitted from the inside of the living body, detecting the measurement light emitted from the inside of the living body, and computing an optical rotation degree based on a change in a polarization state of the measurement light using a detection result of the measurement light and analyzing a concentration of the biological component based on the computed optical rotation degree. The emission and detection of the measurement light are performed by a measurement section configured to detect the measurement light emitted from the living body as a result of scattering of the measurement light inside the living body and then reflection of the measurement light inside the living body. Polarization directions of the measurement light are switched in a time division manner.

According to an aspect of the present disclosure, there is provided a program causing a computer configured to be capable of communicating with a measuring instrument having a light source unit configured to emit measurement light having at least one kind of wavelength for measuring a biological component included inside a living body, a detection unit configured to detect the measurement light emitted from the inside of the living body, and a polarization control unit configured to be provided in at least one position between the light source unit and the living body or between the living body and the detection unit and to control a polarization direction of the measurement light, the measuring instrument detecting the measurement light emitted from the living body as a result of scattering of the measurement light inside the living body and then reflection of the measurement light inside the living body, to execute an analysis function of computing an optical rotation degree based on a change in a polarization state of the measurement light using a measurement result obtained by the measuring instrument and analyzing a concentration of the biological component based on the computed optical rotation degree, and a control function of the measuring instrument.

According to an aspect of the present disclosure, a polarization direction of measurement light is controlled by the polarization control unit during the time in which the measurement light emitted from the light source unit is emitted from a living body and then detected by the detection unit. In addition, the analysis unit uses a measurement result measured by the measurement unit to compute an optical rotation degree based on a change in a polarization state of the measurement light, and thereby to analyze a concentration of a biological component based on the computed optical rotation degree.

Advantageous Effects of Invention

According to the present disclosure described above, it is possible to achieve further miniaturization of a device.

BRIEF DESCRIPTION OF DRAWINGS

FIG. 6 is an illustrative diagram for describing a polarization control unit according to the embodiment.

FIG. 7A is an illustrative diagram for describing a light source unit according to the embodiment.

FIG. 7B is an illustrative diagram for describing a light source unit according to the embodiment.

FIG. 16 is a block diagram showing an example of a hardware configuration of a measurement device according to an embodiment of the present disclosure.

DESCRIPTION OF EMBODIMENT

Hereinafter, a preferred embodiment of the present invention will be described in detail with reference to the appended drawings. Note that, in this specification and the drawings, elements that have substantially the same function and structure are denoted with the same reference signs, and repeated explanation is omitted.

Note that description will be provided in the following order.

(1) Regarding a principle of measurement of a concentration based on an optical rotation degree
(2) First embodiment
(2-1) Regarding a configuration of a measurement device
(3) Regarding a hardware configuration of a measurement device according to an embodiment of the present disclosure

Figure 1:
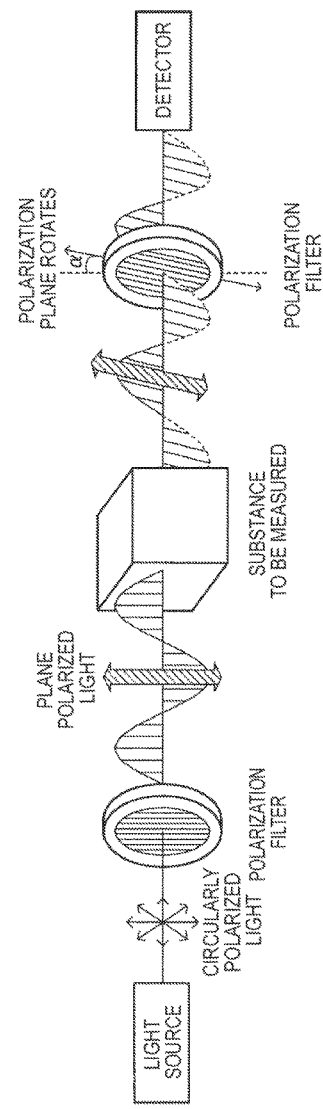
FIG. 1 is an illustrative diagram for describing a principle of measurement of a concentration based on an optical rotation degree.

Regarding a Principle of Measurement of a Concentration Based on an Optical Rotation Degree Prior to describing a measurement device, a measurement method, a program, and a recording medium according to an embodiment of the present disclosure, a principle of measurement of a concentration based on an optical rotation degree will be briefly described below with reference to FIG. 1. FIG. 1 is an illustrative diagram for describing the principle of measurement of a concentration based on an optical rotation degree.

Light is a kind of electromagnetic waves, and an electromagnetic wave that includes light can be considered as a transverse wave oscillating in various orthogonal directions (for example, a longitudinal direction, a lateral direction, a diagonal direction, and the like) to its advancing direction. Among light oscillating in such various directions, there can also be kinds of light oscillating in a specific direction. Such light oscillating in a specific direction is called polarized light. As some kinds of such polarized light, there are circularly polarized light which circles in its oscillating direction according to propagation of light, plane polarization light (also called plane polarized light) oscillating only in a specific direction, and the like. In addition, with regard to the circularly polarized light, it is known that there are two kinds of circularly polarized light, i.e., right-handed circularly polarized light and left-handed circularly polarized light, which differ in a rotation direction (clockwise or counterclockwise). In addition, the plane polarization light can be considered as the vector sum of right-handed circularly polarized light and left-handed circularly polarized light which move forward in the completely same oscillation and cycle.

Next, as shown in FIG. 1, circularly polarized light is assumed to be emitted from a light source. When a polarizer (polarization filter) that is an optical element that can extract specific polarized light (for example, light oscillating only in a longitudinal direction) is installed on the optical path of the circularly polarized light, light that can be transmitted through the polarization filter is only plane-polarized light oscillating in the longitudinal direction as shown in FIG. 1.

Here, a case in which plane polarized light is incident on a substance (measurement substance) as shown in FIG. 1 is considered. When the measurement substance is a solution of a substance having asymmetric carbon such as glucose or a solid such as a crystal having a polarization plane, an interaction occurs between the plane polarized light and the measurement substance, and accordingly, a difference is made between a speed of right-handed circularly polarized light and a speed of left-handed circularly polarized light that move through the substance. In this case, the polarization plane of the plane polarized light considered as the vector sum of the right-handed circularly polarized light and the left-handed circularly polarized light rotates by an angle of a from the polarization plane at the time of incidence. In this case, when a speed of the right-handed circularly polarized light is higher than a speed of the left-handed circularly polarized light, the polarization plane at the time of the incidence on the substance rotates on the right side from the polarization plane at the time of the incidence, and when a speed of the left-handed circularly polarized light is higher than a speed of the right-handed circularly polarized light, the polarization plane at the time of the incidence of the substance rotates on the left side from the polarization plane at the time of the incidence. This phenomenon is called optical rotation and the rotation angle α is called an optical rotation degree.

Here, it is known that a size of an optical rotation degree a measured by a detector is expressed by Formula 10 below using a constant unique to a substance of interest (specific optical rotation degree), a concentration of the substance of interest, and a transmission distance.

[Math. 1]

$$\alpha(\lambda) = [\alpha]_\lambda^t \cdot C \cdot L \qquad \text{Formula 10}$$

Here, in Formula 10 above, the factors have the following meanings:

$\alpha(\lambda)$: an actual measurement value of an optical rotation degree of a substance at a temperature t measured using plane polarized light having a wavelength $\lambda$ $[\alpha]_\lambda^t$: a specific optical rotation degree of a substance at a temperature t measured using plane polarized light having a wavelength $\lambda$ C: a concentration of a substance [g/ml]

L: a transmission distance [mm]

Since a specific optical rotation degree is a value unique to the substance as described above, if the distance light has moved through the substance (the parameter L in Formula 10 above) and an actual measurement value of an optical rotation degree can be obtained, a concentration of a measurement substance of interest can be specified using Formula 10 above.

Focusing on an optical rotation degree expressed by Formula 10, a measurement device according to an embodiment of the present disclosure that will be described hereinbelow computes an optical rotation degree from a change in a polarization state of the polarized light (measurement light) used in the measurement based on a measurement result obtained by measuring a living body using polarized light. Then, the measurement device according to the embodiment of the present disclosure specifies a concentration of a biological component based on the computed optical rotation degree.

First Embodiment

<Regarding a Configuration of a Measurement Device>

Figure 2:
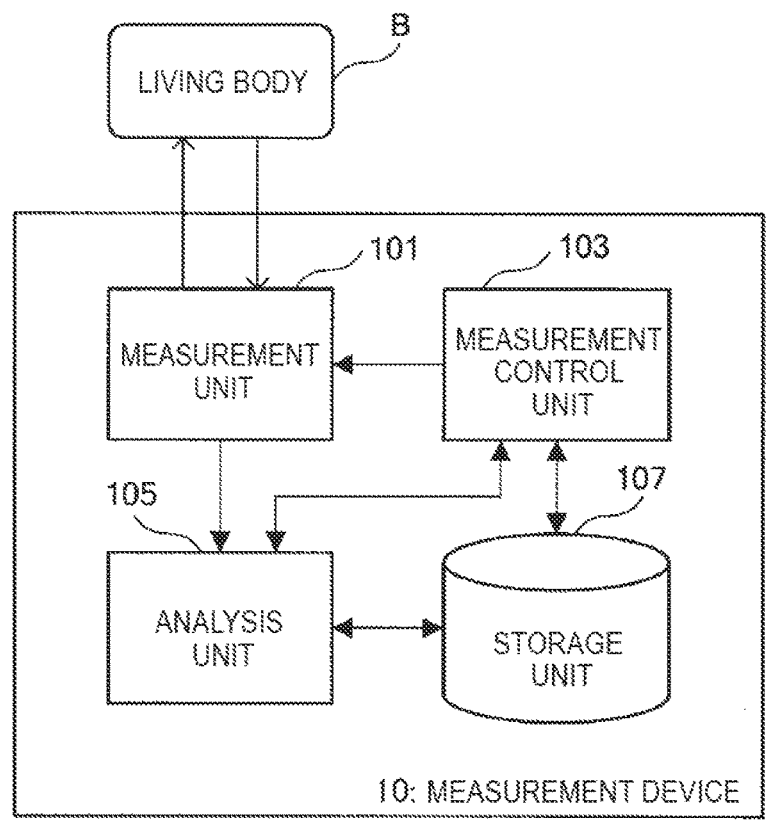
FIG. 2 is a block diagram showing a configuration of a measurement device according to a first embodiment of the present disclosure.
Figure 3A:
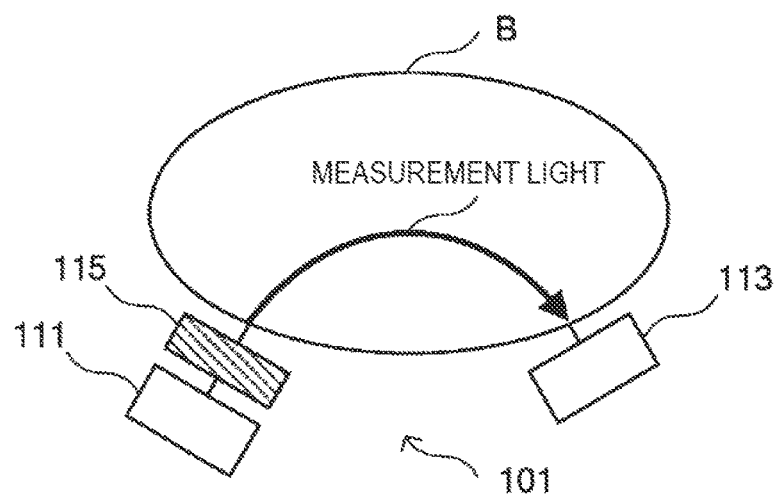
FIG. 3A is an illustrative diagram showing an outline of a measurement unit included in the measurement device according to the embodiment.
Figure 3B:
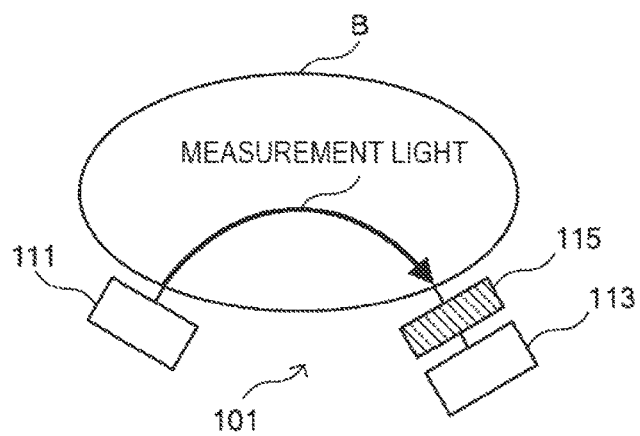
FIG. 3B is an illustrative diagram showing the outline of the measurement unit according to the embodiment.
Figure 3C:
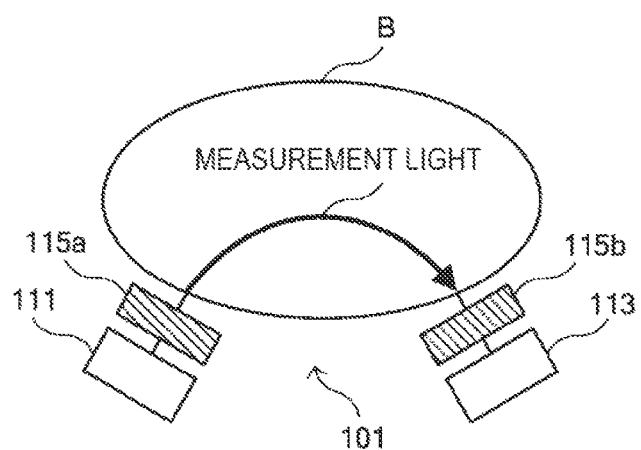
FIG. 3C is an illustrative diagram showing the outline of the measurement unit according to the embodiment.
Figure 4:
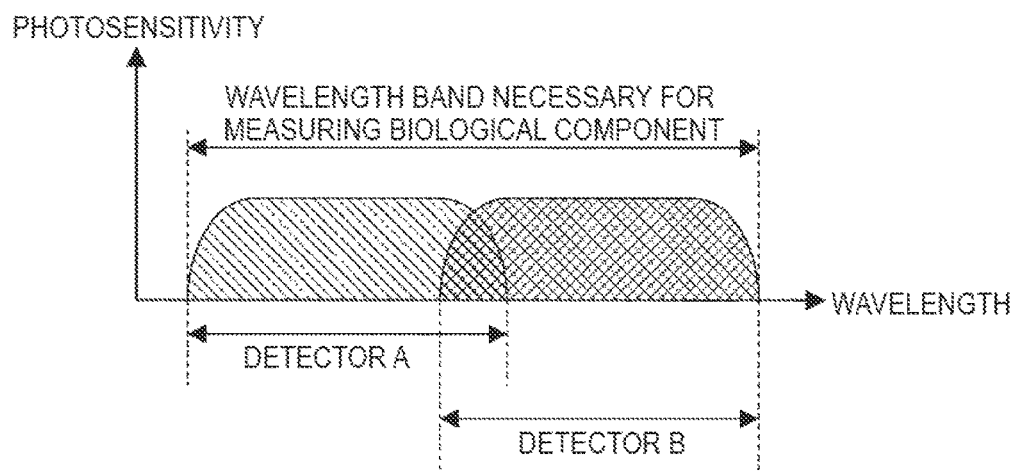
FIG. 4 is an illustrative diagram for describing the measurement unit according to the embodiment.
Figure 5:
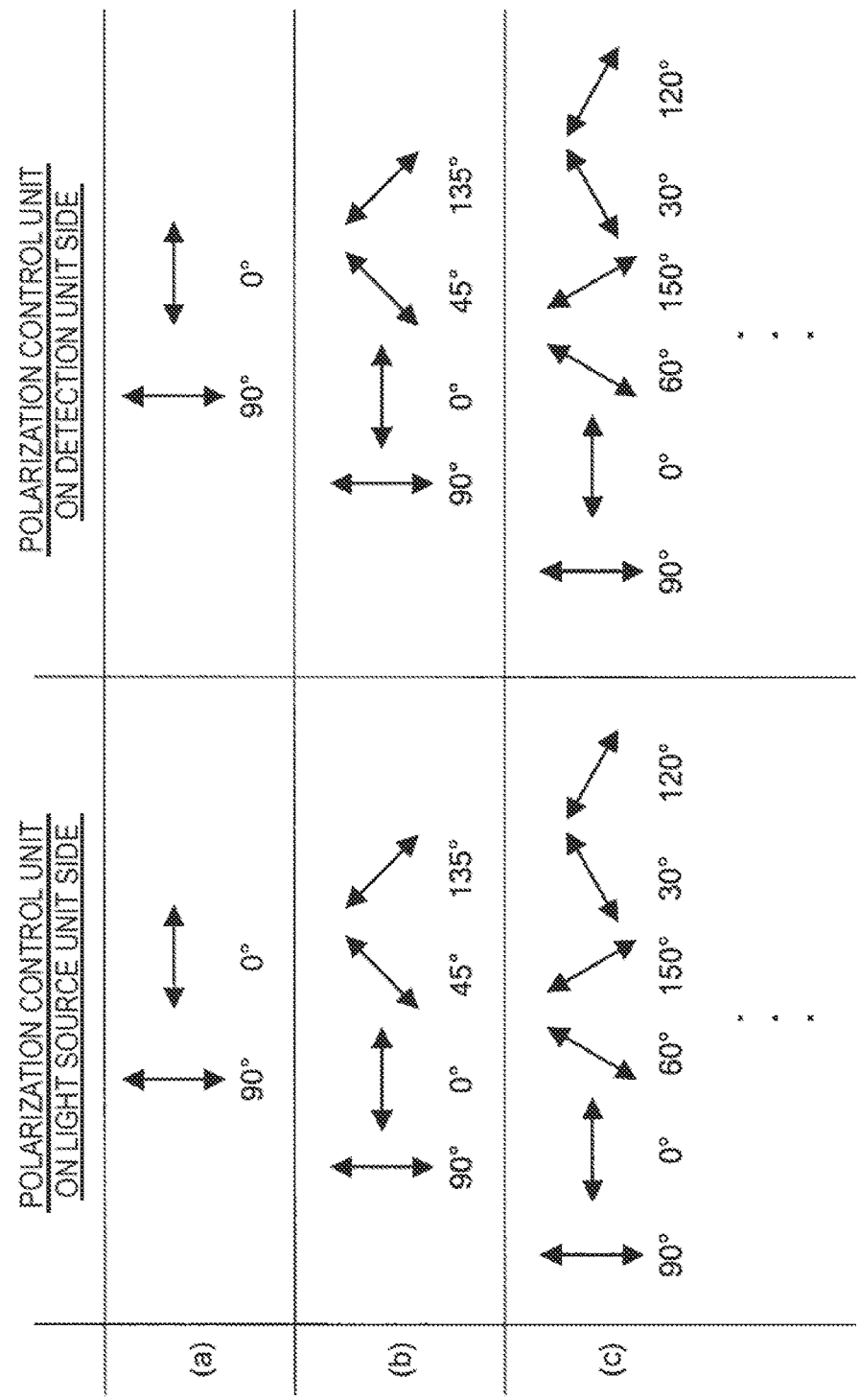
FIG. 5 is an illustrative diagram for describing a polarization control unit according to the embodiment.

Next, a measurement device and a measurement method according to a first embodiment of the present disclosure will be described in detail with reference to FIGS. 2 to 15. FIG. 2 is a block diagram showing a configuration of the measurement device 10 according to the present embodiment. FIGS. 3A to 3C are illustrative diagrams showing an outline of a measurement unit according to the present embodiment. FIG. 4 is an illustrative diagram for describing the measurement unit according to the present embodiment. FIGS. 5 and 6 are illustrative diagrams for describing a polarization control unit according to the present embodiment. FIGS. 7A and 7B are illustrative diagrams for describing a light source unit according to the present embodiment. FIGS. 8 to 14 are illustrative diagrams showing a specific example of the measurement unit according to the present embodiment. FIG. 15 is an illustrative diagram for describing an analysis process performed by an analysis unit according to the present embodiment.

First, a whole configuration of the measurement device 10 according to present embodiment will be described in detail with reference to FIG. 2.

The measurement device 10 according to the present embodiment measures at least a part of a living body B which is a measurement target using at least one kind of measurement light having a predetermined wavelength, and computes a concentration of a biological component included inside the living body based on an obtained measurement result. In this case, the measurement device 10 controls a polarization direction of the measurement light, and computes an optical rotation degree based on a change in a polarization state (a change of the polarization direction) of the detected measurement light. In addition, the measurement device 10 computes a concentration of a biological substance (for example, a concentration of a component in blood such as glucose, albumin, or cholesterol in blood) based on the computed optical rotation degree.

In addition, in the measurement device 10 according to the present embodiment, not only can a concentration of a biological component be analyzed based on the optical rotation degree, but concentrations of various biological components can also be specified through multivariate analysis using information that can be secondarily computed from a measurement result such as a scattering characteristic spectrum or an absorption spectrum obtained from the measurement result.

The measurement device 10 mainly includes a measurement unit 101 that measures a measurement region of the living body B, a measurement control unit 103, an analysis unit 105, and a storage unit 107 as shown in FIG. 2.

[Regarding the Measurement Unit 101]

Hereinafter, a configuration of the measurement unit 101 according to the present embodiment will first be described in detail with reference to FIGS. 3 to 14.

The measurement unit 101 according to the present embodiment mainly includes a light source unit 111, a detection unit 113, and a polarization control unit 115 as shown in FIGS. 3A to 3C.

Regarding the Light Source Unit

The light source unit 111 emits measurement light having at least one kind of wavelength for measuring a biological component included inside a living body.

A wavelength of the measurement light emitted by the light source unit 111 can be arbitrarily set according to a biological component of interest. When oxygenated hemoglobin is measured, for example, near infrared light having a wavelength of 940 nm or so can be used, and when reduced hemoglobin is measured, infrared light having a wavelength of 660 nm or so can be used. In addition, as the light source unit 111 emits light having a wavelength of 940 nm or 950 nm, knowledge relating to fat present in a hypodermal tissue can be obtained. In addition, as the light source unit 111 emits light having a wavelength of 568 nm, 580 nm, 660 nm, or 890 nm, knowledge relating to a melanin pigment can be obtained. In addition, as the light source unit 111 emits light having a plurality of characteristic wavelengths of about 970 nm, 1160 nm, 1250 nm, around 1400 nm, 1550 nm, 1650 nm, and 2200 nm which are peaks of generally-known characteristic spectrums of glucose, 1200 nm, around 1300 nm and 1600 nm, which are characteristic bottoms thereof, in a time division manner, and an obtained detection result is analyzed using various analysis techniques, for example, multivariate analysis and the like, knowledge relating to glucose can be obtained. Such light having a plurality of wavelengths is emitted, for example, in a time division manner from the light source unit 111.

Note that various wavelengths described above are merely exemplary, and the light emitted from the light source unit 111 in the measurement device 10 according to the present embodiment is not limited to the above examples.

The light source unit 111 may use a light emitting diode (LED), a small-sized laser, or the like, for example, and one or a plurality of such light emitting devices are provided for the light source unit 111.

In addition, in the light source unit 111, an emission timing of the measurement light, intensity of the emitted measurement light, switching of a light emitting device when there are a plurality of light emitting devices, and the like are controlled by the measurement control unit 103 that will be described below.

Regarding the Detection Unit

The detection unit 113 detects the measurement light emitted from the inside of the living body B, converts intensity of the detected measurement light into an electrical signal, and then outputs the signal to the analysis unit 105 that will be described below. The detection unit 113 is configured using, for example, a CCD (Charge Coupled Devices) type image sensor, a CMOS (Complementary Metal Oxide Semiconductor) type image sensor, a sensor having a light sensing element of an organic EL, or a TFT (Thin Film Transistor) type image sensor, or a two-dimensional area sensor which is a so-called image sensor. In addition, as the image sensor, a microlens array image sensor having a microlens array (MLA) optical system in which a plurality of microlenses are arrayed in a grid shape can also be used. Note that, as a simplified model, a one-dimensional sensor such as a line sensor can also be installed in the detection unit 113.

In addition, as the detection unit 113, various kinds of optical detectors including a photodiode (PD), an InGaAs detector, and the like can also be used in addition to an image sensor.

In the detection unit 113, a scanning time and the like are controlled by the measurement control unit 103 that will be described later, and detection intensity of measurement light can be output to the analysis unit 105 at an arbitrary timing.

Note that, depending on a biological component of interest in the measurement device 10 according to the present embodiment, there can be a case in which a width of a wavelength band which can be detected by a detector such as an image sensor, a photodiode, or the like is narrower than that of a wavelength band necessary for measuring the biological component of interest. In such a case, the detection unit 113 can also be set using a combination of a plurality of kinds of detectors having different detectable wavelength bands as shown in, for example, FIG. 4. FIG. 4 illustrates that wavelength bands necessary for measuring a biological component are secured using two different kinds of detectors (a detector A and a detector B) while parts of the detectable wavelength bands overlap.

Regarding the Polarization Control Unit

The polarization control unit 115 is an optical element represented by a polarizer, for example, a polarization filter which can control a polarization direction of light used as measurement light, and in the measurement unit 101 according to the present embodiment, at least two kinds of the polarization control unit 115 (polarization filter, and the like) are used so that measurement light turns into at least two kinds of plane polarized light orthogonal to each other.

As shown in FIGS. 3A to 3C, the polarization control unit 115 described above is provided in a position between the light source unit 111 and a living body (which corresponds to FIG. 3A), in a position between a living body and the detection unit 113 (which corresponds to FIG. 3B), or in both positions between the light source unit 111 and a living body and between the living body and the detection unit 113 (which corresponds to FIG. 3C).

By providing the polarization control unit 115 such as a polarization filter in the position between the light source unit 111 and a living body, plane polarized light beams having different polarization directions from each other (at least two kinds of plane polarized light beams orthogonal to each other) can be radiated to the living body. In addition, by providing the polarization control unit 115 such as a polarization filter in the position between the living body and the detection unit 113, a polarization direction of measurement light emitted from the living body that has passed through the inside thereof can be selected, and the measurement light emitted from the living body having different polarization planes can be individually detected by the detection unit 113. In addition, as shown in FIG. 3C, by providing the polarization control units 115 in both positions between the light source unit 111 and the living body and between the detection unit 113 of the living body, a number of combinations of polarization states of the measurement light of interest for the measurement unit 101 can be further increased.

Hereinbelow, description will be provided exemplifying the case of the polarization control units 115 provided in both positions between the light source unit 111 and the living body and between the detection unit 113 of the living body as shown in FIG. 3C.

In the measurement unit 101 according to present embodiment, at least two kinds of the polarization control units 115 (polarization filter and the like) are used so that measurement light turns into at least two kinds of plan polarization light beams orthogonal to each other as previously described. In addition, in the measurement unit 101 according to the present embodiment, in addition to the two kinds of plane polarized light beams orthogonal to each other, the polarization control unit 115 that can select still another polarization direction may be used so that a plane polarized light beam different from the two kinds of plane polarized light beams orthogonal to each other (in other words, so that the two kinds of polarization directions orthogonal to each other are interpolated). In other words, in the measurement unit 101 according to the present embodiment, a plurality of polarization filters can be appropriately combined so that a combination of proper polarization light beams for obtaining measurement data valid in analysis is realized FIG. 5 shows an example of combinations of polarization directions when a plurality of polarization control units having different polarization directions are used. As shown in FIG. 5(a), as the polarization control unit 115 according to the present embodiment, two kinds of polarization filters are used so that measurement light becomes at least two plane polarized light beams orthogonal to each other (for example, polarization filters which correspond to two kinds of polarization directions of a 0° direction and a 90° direction). In addition, in the present embodiment, polarization filters that can select polarization directions positioned between the two kinds of directions may be used so that the two kinds of polarization directions orthogonal to each other are interpolated as shown in, for example FIG. 5(b) and FIG. 5(c). In other words, the example shown in FIG. 5(b) shows a case in which, in addition to the polarization filter corresponding to the 0° direction and the polarization filter corresponding to the 90° direction, a polarization filter corresponding to a 45° direction and a polarization filter corresponding to a 135° direction are used. In addition, the example shown in FIG. 5(c) shows a case in which, in addition to the polarization filter corresponding to the 0° direction and the polarization filter corresponding to the 90° direction, polarization filters corresponding to 30°, 60°, 120°, and 150° are used.

As shown in FIGS. 5(b) and 5(c), by using more polarization filters so as to interpolate polarization directions orthogonal to each other, when the analysis unit 105 that will be described below specifies an optical rotation degree, it is possible to specify an optical rotation degree more accurately.

In addition, as shown in FIG. 5, the polarization control unit 115 provided in the position between the light source unit 111 and the living body and the polarization control unit 115 provided in the position between the living body and the detection unit 113 are set so that selectable polarization planes form a pair at angles of, for example, 0° and 0°, and 90° and 90°. However, in the measurement unit 101 according to the present embodiment, a polarization direction selected by the polarization control unit 115 provided in the position between the living body and the detection unit 113 may be set so that the direction rotates by a predetermined offset angle with respect to a polarization direction selected by the polarization control unit 115 provided in the position between the light source unit 111 and the living body as shown in, for example, FIG. 6. By setting angles of the polarization control unit (polarization filters) 115 provided in two positions so as to deviate from each other as shown in FIG. 6, many polarization states can be selected while reducing the number of polarization filters to be used.

In addition, by setting an installation angle of the polarization control unit 115 provided in the position between the light source unit 111 and the living body to be different from an installation angle of the polarization control unit 115 provided in the position between the living body and the detection unit 113, it is possible to prevent light to be detected from being blacked out by the polarization control unit 115. Accordingly, when an arithmetic operation is performed based on signal intensity in the analysis unit 105 that will be described below, it is possible to avoid a situation of performing division by zero (in other words, a result of the arithmetic operation becomes indefinite) and accordingly, analysis accuracy can be enhanced.

Hereinabove, the measurement unit 101 according to the present embodiment has been described in detail with reference to FIGS. 3A to 6.

Regarding Control of Polarized Light Having a Plurality of Wavelengths

As described above, in the measurement unit 101 according to the present embodiment, light having a plurality of wavelengths with a plurality of kinds of polarization planes can be used as measurement light for analyzing a concentration of a biological component. Hereinbelow, a control method of measurement light having such a plurality of wavelengths with a plurality of polarization plans will be briefly described with reference to FIGS. 7A and 7B. Note that description will be provided below exemplifying a case in which measurement light having three kinds of wavelengths (970 nm, 1200 nm, and 1650 nm) with two kinds of polarization directions of a polarization direction A and a polarization direction B is used.

In the measurement unit 101 according to the present embodiment, when six kinds of plane polarized light beams which are beams of two kinds of polarization directions× three kinds of wavelengths are radiated to a living body, the six kinds of plane polarized light beams can be radiated in a time division manner by sequentially switching combinations of the light source and the polarization filters as shown in FIG. 7A.

Here, if the number of kinds of wavelengths of light used as measurement light increases, there is a possibility of an obtained detection signal losing its peak shape. Thus, accuracy of the obtained detection signal can be enhanced by performing the switching of the plane polarized light beams to be radiated at random as shown in FIG. 7B, rather than performing the switching with regularity as shown in FIG. 7A. This is because data having a frequency higher than a sampling frequency can be detected by performing the switching at random. By performing such control, accuracy of a waveform shape can be enhanced, and more correct measurement can be performed when the analysis unit 107 that will be described later computes a temporal change of the detection signal (i.e., a pulse waveform or the like) as secondary information and uses the data in analysis of the biological component.

Regarding a Specific Example of the Measurement Unit

Next, specific examples of the measurement unit 101 according to the present embodiment will be described with reference to FIGS. 8 to 14.

First, a specific example of the measurement unit 101 shown in FIG. 8 will be described. The measurement unit 101 shown in FIG. 8 has two sections including a radiation section that radiates measurement light to a living body and a detection section that detects the measurement light emitted from the living body. The measurement unit 101 forms a so-called reflection and scattering type measurement section that detects measurement light emitted from the living body B as a result of reflection and scattering of the measurement light that occurred inside the living body. In such a reflection and scattering type measurement section, the measurement light moves through the living body B in substantially a U shape and then is detected by the detection unit 113.

Figure 8:
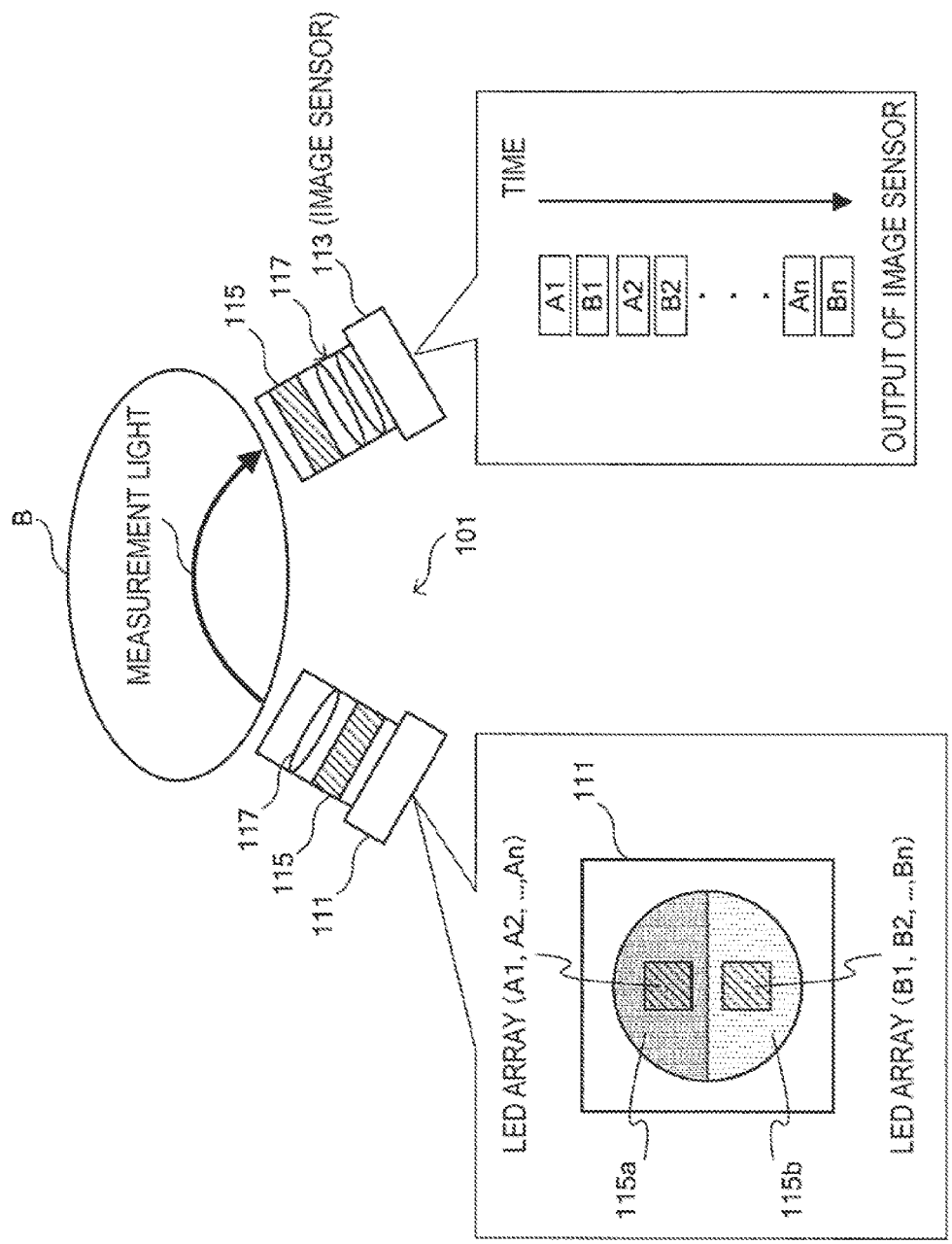
FIG. 8 is an illustrative diagram showing a specific example of the measurement unit according to the embodiment.

In the example shown in FIG. 8, as the light source unit 111, two identical LED arrays that can emit light of n kinds of wavelengths 1 to n are used, and on the LED arrays, polarization filters (polarization filters 115a and 115b) that can select different polarization directions are provided. In addition, the measurement light that has been transmitted through the polarization filter 115 is transmitted through an object lens 117 and then is radiated to the living body B.

A polarization direction of the measurement light that has penetrated the inside of the living body B along the substantially U-shaped path is selected by a polarization filter 115 on the detection unit 113 side (to be more specific, the same polarization filters 115a and 115b as the polarization filter on the light source unit 111 side). Then, the measurement light that has been transmitted through the polarization filter 115 is collected by the object lens 117, and forms an image in an image sensor functioning as the detection unit 113.

The image sensor acquires a detection result of each plane polarized light beam at a timing synchronized with the light source unit 111 and outputs the detection result to the analysis unit 107 as shown on the right side of FIG. 8.

As shown on the left side of FIG. 8, in the present specific example, light source groups set to have predetermined plane polarized light using combinations of the LED arrays and the polarization filters are provided, and the light source groups are electrically switched to be used. Accordingly, an LED array (A1, A2, . . . An) that can emit n kinds of measurement light beams having a certain polarized light beam (for example, plane polarized light in the 0° direction) and an LED array (B1, B2, . . . Bn) that can emit n kinds of measurement light beams having a polarized light beam (for example, plane polarized light in the 90° direction) different from the former LED array can be realized. By using such a radiation section, measurement light beams having different polarization planes can be emitted in a time division manner.

Figure 9:
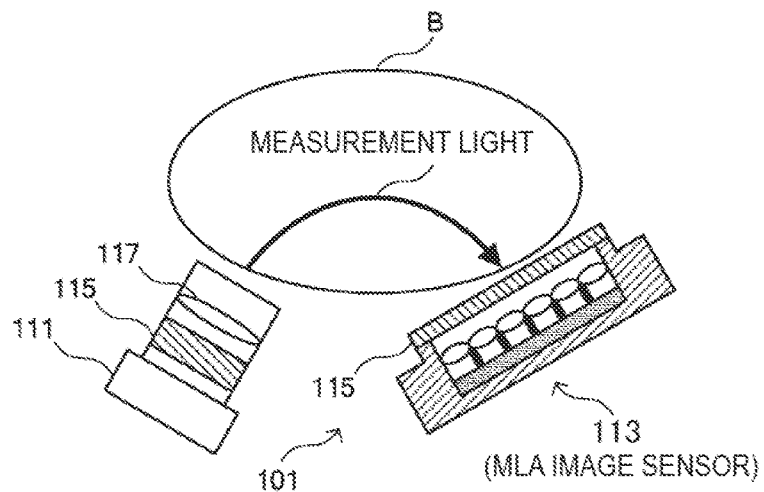
FIG. 9 is an illustrative diagram showing a specific example of the measurement unit according to the embodiment.

In the example shown in FIG. 8, a general image sensor is used in the detection section, but a microlens array (MLA) image sensor provided with the polarization filter 115 can also be used as the detection section as shown in FIG. 9. Here, the radiation section shown in FIG. 9 has the same configuration as in the example shown in FIG. 8.

The MLA image sensor is an image sensor having a microlens array optical system. The microlens array is constituted by a plurality of microlenses which are light sensing lenses, and the microlenses are each arrayed on a predetermined substrate in a grid shape. Each of the microlenses guides the measurement light incident on the microlenses to the image sensor.

Since the microlens is a lens array having little curvature of field and no distortion in a depth direction, by using such a microlens array, satisfactory measurement data can be obtained. Note that a depth of field of each microlens constituting the microlens array is set so that a skin structure of interest in the measurement device 10 according to the present embodiment is included (for example, focus is on in the range of a depth of several millimeters to dozens of millimeters from the epidermis) even when the living body B is present at a close distance.

In the MLA image sensor, a light shielding body is provided between adjacent microlenses, and thereby directivity of light is controlled, and crosstalk of detected light beams between microlenses can be prevented. In addition, signals can be selectively acquired from one or a plurality of pixels of the image sensor corresponding to each microlens. For this reason, detected signals having excellent spatial resolution and time resolution can be acquired using the MLA image sensor.

Figure 10:
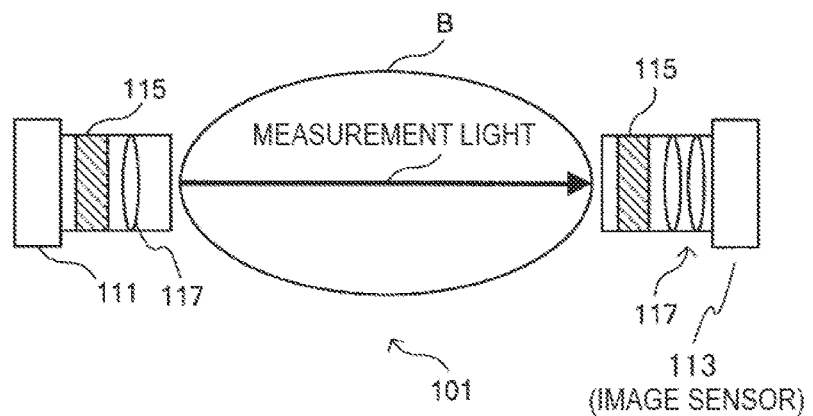
FIG. 10 is an illustrative diagram showing a specific example of the measurement unit according to the embodiment.

FIG. 10 shows an example in which the radiation section and the detection section shown in FIG. 8 are used as a transmission type measurement section in which the units are disposed so as to face each other while setting a living body B to be interposed between the units and measurement light that has been completely transmitted through the inside of the living body is detected. In the case of the transmission type measurement section, the MLA image sensor can also be used as shown in FIG. 11.

Figure 11:
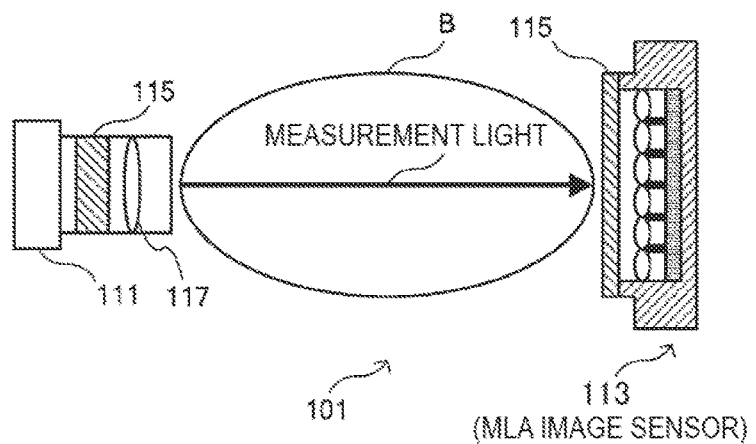
FIG. 11 is an illustrative diagram showing a specific example of the measurement unit according to the embodiment.

Here, by using a reflection and scattering type measurement section as shown in FIGS. 8 and 9, rather than using the transmission type measurement section as shown in FIGS. 10 and 11, a length of a path along which measurement light penetrates inside a living body can be set to be shorter than in the case of the transmission type measurement. By setting the distance in which the measurement light penetrates inside the living body to be short, a degree of absorption or scattering of the measurement light caused by various biological components present in the living body can be reduced. As a result, detection of a biological component is possible in a wavelength band of 1000 nm or higher which was difficult in the transmission scheme, and even when a substance, for example, glucose, of which temperature greatly changes is measured, it is possible to reduce an influence of changes overlapping in measurement results. Furthermore, since a percentage of a light amount emitted from a living body increases even when a light source with a low light amount that has low light emission intensity is used, it is possible to reduce the amount of electric power consumed in the light source in comparison to the past.

Figure 12:
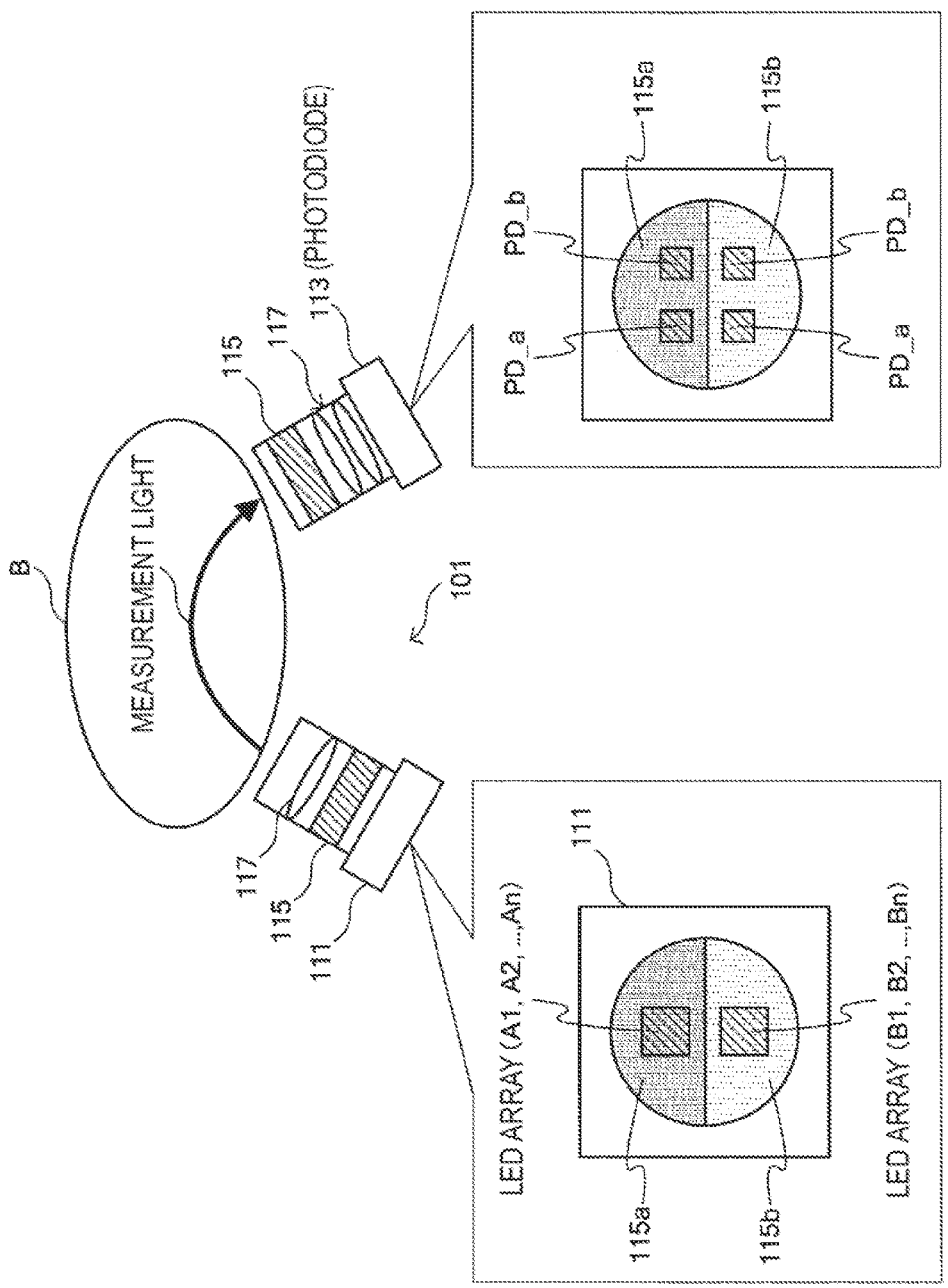
FIG. 12 is an illustrative diagram showing a specific example of the measurement unit according to the embodiment.

In addition, in the examples shown in FIGS. 8 to 11, the image sensor is used as the detection unit 113, but as shown in FIG. 12, photodiodes (PD) can also be used as the detection unit 113. FIG. 12 shows a specific example of the measurement unit 101 when photodiodes are used as the detection unit 113.

A structure of the radiation section shown on the left side of FIG. 12 in the measurement unit 101 shown in FIG. 12 is the same as that of the radiation section shown in FIG. 8, and thus detailed description thereof will be omitted below.

The detection section of the measurement unit 101 shown in FIG. 12 has a polarization filter 115 that corresponds to the polarization filter 115 (polarization filters 115a and 115b) in the radiation section, an object lens 117, and photodiodes functioning as the detection unit 113 as shown on the right side of FIG. 12.

In the example shown in FIG. 12, two kinds of photodiodes PD_a and PD_b having different wavelength bands are used as photodiodes as described with reference to FIG. 4. Using two sets of photodiode groups constituted by the two kinds of photodiodes, one set of each of the photodiode groups is disposed below one of the polarization filters 115a and 115b. Accordingly, a component in a certain polarization direction (for example, plane polarized light in the 0° direction) of measurement light to be detected is detected by the photodiodes PD_a and PD_b provided below the polarization filter 115a, and a component in a different polarization direction (for example, plane polarized light in the 90° direction) thereof is detected by the photodiodes PD_a and PD_b provided below the polarization filter 115b.

Figure 13:
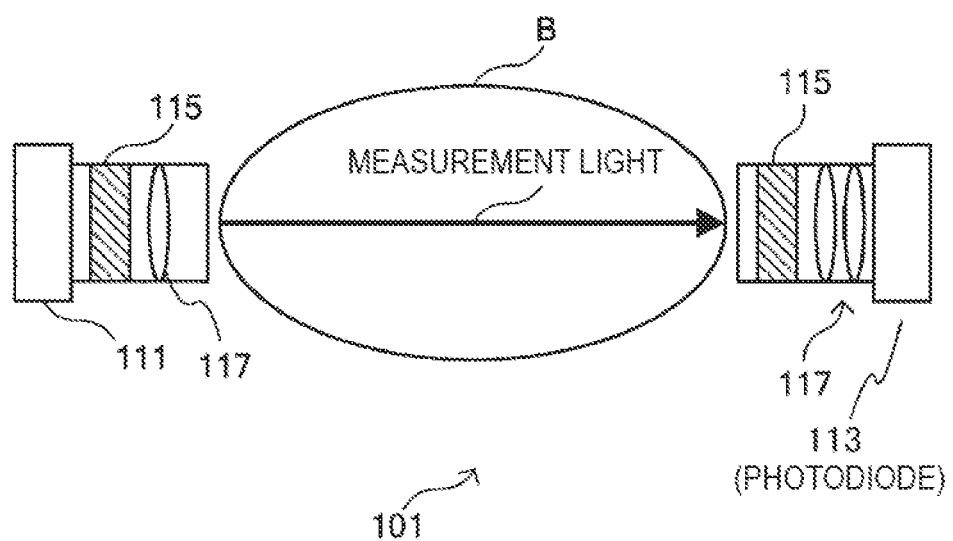
FIG. 13 is an illustrative diagram showing a specific example of the measurement unit according to the embodiment.

In the example shown in FIG. 12, the reflection and scattering type measurement section is illustrated, but as shown in FIG. 13, for example, the radiation section and the detection section shown in FIG. 12 may also form a transmission type measurement section with the units disposed to face each other and a living body set therebetween.

Figure 14:
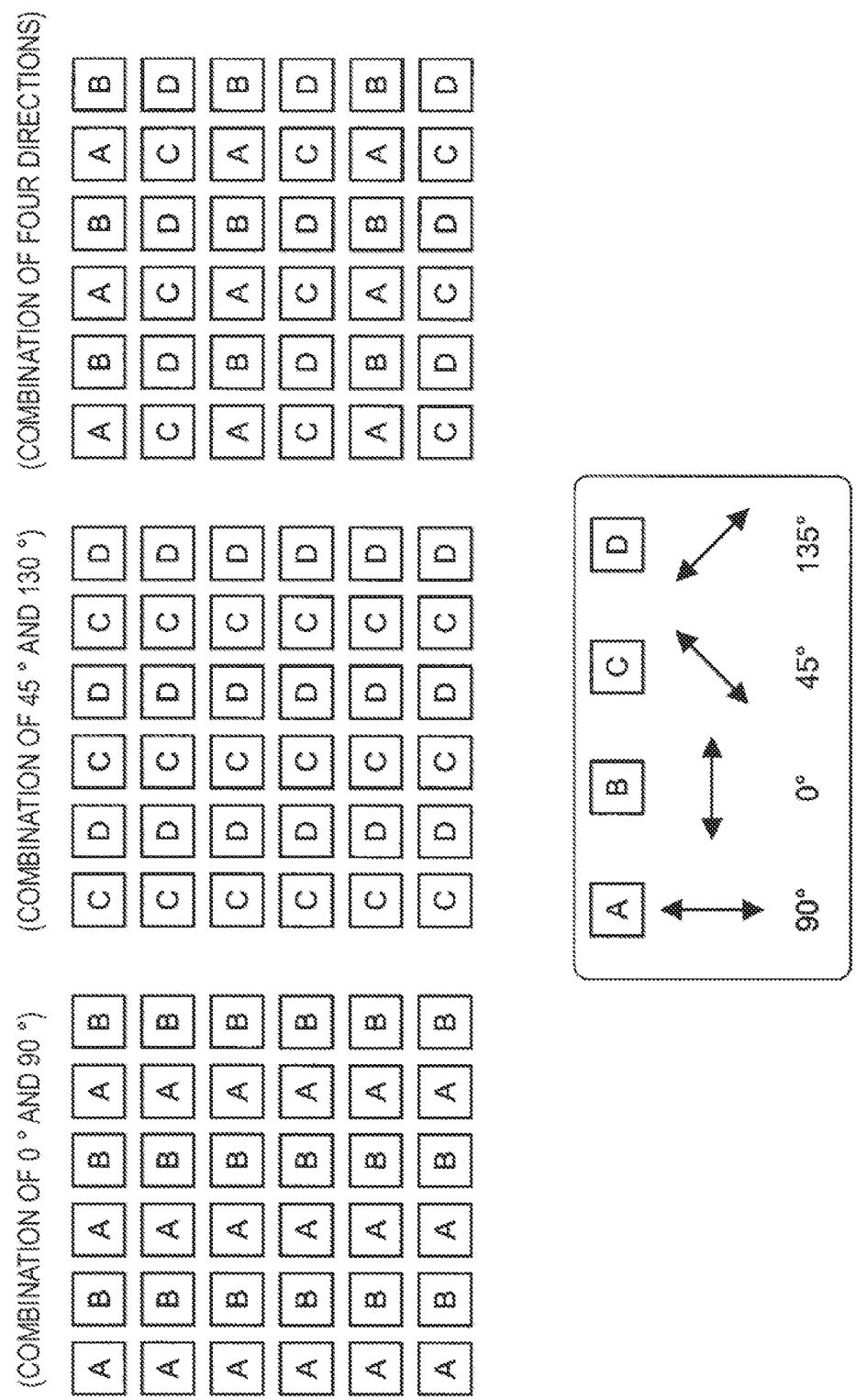
FIG. 14 is an illustrative diagram showing a specific example of the measurement unit according to the embodiment.
Figure 15:
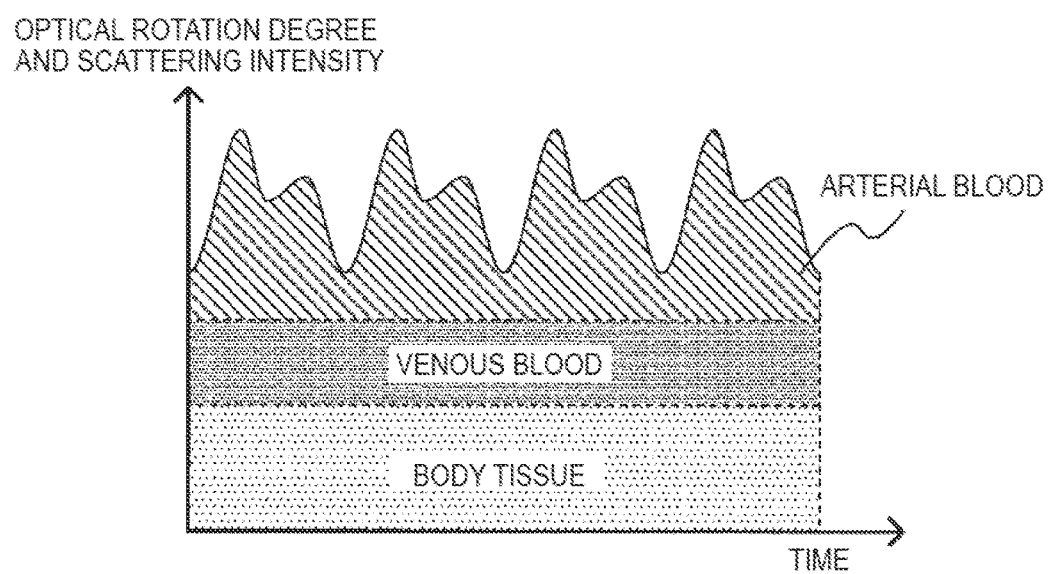
FIG. 15 is an illustrative diagram for describing an analysis process performed in an analysis unit according to the embodiment.

In addition, in the examples shown in FIGS. 8 to 13, the case in which the polarization filters serving as the polarization control unit 115 are disposed above the detection unit 113 has been described, but as shown in FIG. 14, for example, a polarization direction of light to be sensed can also be selected for each pixel of an image sensor. In other words, when polarization filters for each pixel are disposed as shown in FIG. 14, plane polarized light beams having different polarization planes can be simultaneously measured with one image sensor. In this case, the polarization filters may be disposed on pixels of the image sensor as shown in FIG. 14 such that a combination of any two kinds of polarization directions may be realized on pixels of the image sensor, or a combination of four kinds of polarization directions may be realized.

As described above, in the measurement device 10 according to the present embodiment, since the polarization directions of light used as measurement light are electrically switched and then used in measurement of a biological component, further miniaturization of the device can be achieved than in a measurement device using a non-invasive optical scheme of the past. In addition, by employing a reflection and scattering type optical system as the measurement unit 101, further miniaturization of the device can be achieved, and convenience of a person to be measured can also be enhanced.

The measurement unit 101 included in the measurement device 10 according to the present embodiment has been described in detail above with reference to FIGS. 2 to 14.

[Regarding the Measurement Control Unit 103]

Returning to FIG. 2 again, the measurement control unit 103 included in the measurement device 10 according to the present embodiment will be described.

The measurement control unit 103 is realized by, for example, a CPU (Central Processing Unit), a ROM (Read Only Memory), a RAM (Random Access Memory), and the like. The measurement control unit 103 takes overall charge of the measurement process of the living body B performed in the measurement unit 101 by performing drive control of the light source unit 111 and the detection unit 113, control of the polarization control unit 115, and the like provided in the measurement unit 101. To be more specific, the measurement control unit 103 performs drive control of the detection unit such as selection of the detection unit 113 for acquiring a scanning timing of the detection unit 113, acquiring information, and the like based on a predetermined synchronization signal, and the like. In addition, the measurement control unit 103 also performs switching control of switching a light source, and drive control relating to an emission timing and intensity of measurement light with regard to the light source unit 111.

As the measurement control unit 103 performs such control as described above, the light source unit 111 of the measurement unit 101 can emit measurement light beams having different wavelengths and different polarization directions in a time division manner, and can acquire measurement data of an arbitrary position on the detection unit 113 in a time division manner.

The measurement data measured by the measurement unit 101 controlled by the measurement control unit 103 is output to the analysis unit 105 that will be described below, and accordingly, an analysis process of the measurement data is executed.

Here, when the control unit 103 performs control of the measurement unit 101, the control unit can refer to various kinds of programs, parameters, databases, and the like recorded in the storage unit 107 that will be described later.

[Regarding the Analysis Unit 105]

The analysis unit 105 included in the measurement device 10 according to the present embodiment is realized by, for example, a CPU, a ROM, a RAM, and the like. The analysis unit 105 computes an optical rotation degree based on a change in a polarization state of measurement light using a measurement result obtained by the measurement unit 101 and thereby analyzes a concentration of a biological component based on the computed optical rotation degree.

As previously described, by using the polarization control unit 115 such as a polarization filter or the like in the measurement unit 101 according to the present embodiment, it is possible to measure to what extent a component of plane polarized light having a polarization direction defined by the polarization control unit 115 such as a polarization filter is included in measurement light detected by the detection unit 113. Thus, in the analysis unit 105 according to the present embodiment, polarization directions of light and percentages at which they are mixed can be specified using a rate of detection intensity (rate of a sensor gain) of each plane polarized light beams detected by the detection unit 113. If such a rate can be obtained, by performing vector calculation (a process of combining vectors) based on the obtained rate and a vector indicated by each polarization direction defined by the polarization filter, the analysis unit 105 can specify a direction of a polarization plane of the detected measurement light. The analysis unit 105 can compute an optical rotation degree based on information of measurement light of the polarization direction that was used to measure a measurement result of interest which had been acquired from the measurement control unit 103 (information obtained from the timing chart of time division as shown in FIG. 7A, 7B, or the like) and the obtained direction of the polarization plane.

When the analysis unit 105 has computed the optical rotation degree using the method described above, the analysis unit computes a concentration of the biological component of interest (for example, glucose, albumin, or cholesterol in blood or the like) based on Formula 10 described above with reference to a specific optical rotation degree of the biological component of interest stored in the storage unit 107 or the like.

Here, in order to compute the concentration of the biological component based on Formula 10 described above, it is necessary to use a transmission distance L of light, but for the transmission distance L, a constant set in advance referring to an interval between the light source unit 111 and the detection unit 113 in the measurement unit 101 can be used.

In addition, by using each of measurement results obtained when measurement light beams having various wavelengths are used in addition to the optical rotation degree described above, the analysis unit 105 can obtain a scattering characteristic spectrum or an absorption spectrum. Thus, by further using the scattering characteristic spectrum or the absorption spectrum, the analysis unit 105 can compute concentrations of various biological components. In this case, the analysis unit 105 may compute the concentrations of the biological components of interest based on a predetermined arithmetic formula, or may compute the concentrations of the biological components of interest by performing so-called multivariate analysis.

In addition, the analysis unit 105 can separate scattered light scattered inside a living body and transmitted light that has been transmitted through the living body (in other words, light that moves straight through the living body) based on a polarization plane of measurement light emitted toward the living body and a polarization plane of the measurement light emitted from the living body. Such a process of separating scattered light and transmitted light can be performed based on polarization planes of measurement light beams of wavelengths used as measurement light.

In addition, also in the measurement scheme according to the present embodiment described above, only a component in arterial blood can be extracted using a temporal change of the component in arteries in the same manner as the known scheme that uses light absorptance of a substance. As represented by a pulse oximeter in the past, a signal which has penetrated inside the living body B from the light source unit 111 and then been detected by the detection unit 113 includes a quantitative change of arterial blood which has been affected by beats (pulsation) of arteries. Thus, by extracting such a quantitative change of arterial blood as a pulse waveform as shown in, for example, FIG. 15, the analysis unit 105 can estimate oxygen saturation in arterial blood and the like based on the known method.

In addition, by causing the measurement control unit 103 and the analysis unit 105 to be associated with each other and combining measurement light beams having a plurality of kinds of wavelengths and thereby executing time division sampling using a high-speed multi-wavelength light source to emit the measurement light beams having the plurality of kinds of wavelengths in a time division manner, the analysis unit 105 can also estimate a concentration of another biological component in arterial blood such as glucose. To be specific, by focusing on temporal changes of optical rotation degrees computed based on measurement results of the measurement light beams having the wavelengths and a temporal change of a scattering characteristic spectrum, the analysis unit 105 can obtain data indicating a pulse waveform as shown in, for example, FIG. 15. Using a peak value and bottom value of the obtained data indicating the pulse waveform, the analysis unit 105 can estimate a concentration of a biological component in arterial blood (for example, a concentration of glucose, a concentration of albumin, a concentration of cholesterol, or the like) using the known method.

When a component in blood such as glucose is measured focusing on light absorptance of a substance, there is also a component showing very wild temperature fluctuations among such components in blood, and thus the method has been difficult to put into practical use. However, as in the measurement scheme according to the present embodiment, a component in blood showing very wild temperature fluctuations can be stably separated using a scattering characteristic and an optical rotation degree showing a higher change rate.

[Storage unit 107]

Returning to FIG. 2, the storage unit 107 provided in the measurement device 10 according to the present embodiment will be described.

The storage unit 107 is realized by the RAM, a storage device, or the like provided in the measurement device 10 according to the present embodiment. The storage unit 107 stores therein various data used for the analysis processing in the analysis unit 105, a look-up table of various databases, and the like. The storage unit 107 may store therein measurement data measured by the measurement unit 101 according to the present embodiment, various programs or parameters or items of data used for the processing performed by the measurement control unit 103 or the analysis unit 105 according to the present embodiment, and the like. The storage unit 107 can store, in addition to the above data, various parameters, processing progresses, and the like which need to be stored for any processing of the measurement device 10, as needed. Each processing unit such as the measurement unit 101, the measurement control unit 103 or the analysis unit 105 can freely access the storage unit 107 and can write or read data in or from the storage unit 107.

The structure of the measurement device 10 according to the present embodiment has been described above in detail with reference to FIG. 2 to FIG. 15.

The measurement control unit 103 and the analysis unit 105 according to the present embodiment may be part of the measurement device 10 according to the present embodiment, or may be realized by an external device such as computer connected to the measurement device 10. Measurement data generated by the measurement unit 101 is stored in a removable storage medium and the storage medium is removed from the measurement device 10 to be connected to other device having the analysis unit 105, and thus the measurement data may be analyzed.

Heretofore, an example of the functions of the measurement device 10 according to the present embodiment has been shown. Each of the structural elements described above may be configured using a general-purpose material or a general-purpose circuit, or may be configured from hardware dedicated to the function of each structural element. Also, a CPU or the like may perform all the functions of the structural elements. Accordingly, the configuration to be used can be changed as appropriate according to the technical level at the time of carrying out the present embodiment.

Additionally, a computer program for realizing each function of the measurement device according to the present embodiment as described above can be created, and the computer program can be implemented in a personal computer or the like. A recording medium in which such computer program is stored and which can be read by a computer can also be provided. The recording medium is a magnetic disk, an optical disk, a magneto-optical disk, a flash memory, or the like, for example. Also, the computer program may be distributed via a network, for example, without using a recording medium.

(Hardware Configuration)

Next, the hardware configuration of the measurement device 10 according to the embodiment of the present disclosure will be described in detail with reference to FIG. 16. FIG. 16 is a block diagram for illustrating the hardware configuration of the measurement device 10 according to the embodiment of the present disclosure.

The measurement device 10 mainly includes a CPU 901, a ROM 903, and a RAM 905. Furthermore, the measurement device 10 also includes a host bus 907, a bridge 909, an external bus 911, an interface 913, a sensor 914, an input device 915, an output device 917, a storage device 919, a drive 921, a connection port 923, and a communication device 925.

The CPU 901 serves as an arithmetic processing apparatus and a control device, and controls the overall operation or a part of the operation of the measurement device 10 according to various programs recorded in the ROM 903, the RAM 905, the storage device 919, or a removable recording medium 927. The ROM 903 stores programs, operation parameters, and the like used by the CPU 901. The RAM 905 primarily stores programs that the CPU 901 uses and parameters and the like varying as appropriate during the execution of the programs. These are connected with each other via the host bus 907 configured from an internal bus such as a CPU bus or the like.

The host bus 907 is connected to the external bus 911 such as a PCI (Peripheral Component Interconnect/Interface) bus via the bridge 909.

The sensor 914 is detecting means for detecting biological information unique to a user or various types of information to be used to acquire such biological information. This sensor 914 includes, for example, various image sensors such as a CCD (Charge Coupled Device) or a CMOS (Complementary Metal Oxide Semiconductor) and the like. In addition, the sensor 914 may further have optics such as a lens to be used to image an organism site or a light source and the like. The sensor 914 may also be a microphone and the like for acquiring sound and the like. Note that in addition to those mentioned above, the sensor 914 may also include various measuring instruments such as a thermometer, an illuminance meter, a hygrometer, a speedometer, an accelerometer, and the like.

The input device 915 is an operation means operated by a user, such as a mouse, a keyboard, a touch panel, buttons, a switch and a lever. Also, the input device 915 may be a remote control means (a so-called remote control) using, for example, infrared light or other radio waves, or may be an externally connected apparatus 929 such as a mobile phone or a PDA conforming to the operation of the measurement device 10. Furthermore, the input device 915 generates an input signal based on, for example, information which is input by a user with the above operation means, and is configured from an input control circuit for outputting the input signal to the CPU 901. The user of the measurement device 10 can input various data to the measurement device 10 and can instruct the measurement device 10 to perform processing by operating this input device 915.

The output device 917 is configured from a device capable of visually or audibly notifying acquired information to a user. Examples of such device include display devices such as a CRT display device, a liquid crystal display device, a plasma display device, an EL display device and lamps, audio output devices such as a speaker and a headphone, a printer, a mobile phone, a facsimile machine, and the like. For example, the output device 917 outputs a result obtained by various processing performed by the measurement device 10. More specifically, the display device displays, in the form of texts or images, a result obtained by various processes performed by the measurement device 10. On the other hand, the audio output device converts an audio signal such as reproduced audio data and sound data into an analog signal, and outputs the analog signal.

The storage device 919 is a device for storing data configured as an example of a storage unit of the measurement device 10 and is used to store data. The storage device 919 is configured from, for example, a magnetic storage device such as a HDD (Hard Disk Drive), a semiconductor storage device, an optical storage device, or a magneto-optical storage device. This storage device 919 stores programs to be executed by the CPU 901, various data, and various data obtained from the outside.

The drive 921 is a reader/writer for recording medium, and is embedded in the measurement device 10 or attached externally thereto. The drive 921 reads information recorded in the attached removable recording medium 927 such as a magnetic disk, an optical disk, a magneto-optical disk, or a semiconductor memory, and outputs the read information to the RAM 905. Furthermore, the drive 921 can write in the attached removable recording medium 927 such as a magnetic disk, an optical disk, a magneto-optical disk, or a semiconductor memory. The removable recording medium 927 is, for example, a DVD medium, an HD-DVD medium, or a Blu-ray medium. The removable recording medium 927 may be a CompactFlash (CF; registered trademark), a flash memory, an SD memory card (Secure Digital Memory Card), or the like. Alternatively, the removable recording medium 927 may be, for example, an IC card (Integrated Circuit Card) equipped with a non-contact IC chip or an electronic appliance.

The connection port 923 is a port for allowing devices to directly connect to the measurement device 10. Examples of the connection port 923 include a USB (Universal Serial Bus) port, an IEEE1394 port, a SCSI (Small Computer System Interface) port, and the like. Other examples of the connection port 923 include an RS-232C port, an optical audio terminal, an HDMI (High-Definition Multimedia Interface) port, and the like. By the externally connected apparatus 929 connecting to this connection port 923, the measurement device 10 directly obtains various data from the externally connected apparatus 929 and provides various data to the externally connected apparatus 929.

The communication device 925 is a communication interface configured from, for example, a communication device for connecting to a communication network 931. The communication device 925 is, for example, a wired or wireless LAN (Local Area Network), Bluetooth (registered trademark), a communication card for WUSB (Wireless USB), or the like. Alternatively, the communication device 925 may be a router for optical communication, a router for ADSL (Asymmetric Digital Subscriber Line), a modem for various communications, or the like. This communication device 925 can transmit and receive signals and the like in accordance with a predetermined protocol such as TCP/IP on the Internet and with other communication devices, for example. The communication network 931 connected to the communication device 925 is configured from a network and the like, which is connected via wire or wirelessly, and may be, for example, the Internet, a home LAN, infrared communication, radio wave communication, satellite communication, or the like.

Heretofore, an example of the hardware configuration capable of realizing the functions of the measurement device 10 according to the embodiment of the present disclosure has been shown. Each of the structural elements described above may be configured using a general-purpose material, or may be configured from hardware dedicated to the function of each structural element. Accordingly, the hardware configuration to be used can be changed as appropriate according to the technical level at the time of carrying out the present embodiment.

The preferred embodiment of the present disclosure has been described above with reference to the accompanying drawings, whilst the present disclosure is not limited to the above examples, of course. A person skilled in the art may find various alterations and modifications within the scope of the appended claims, and it should be understood that they will naturally come under the technical scope of the present disclosure.

Additionally, the present technology may also be configured as below.

(1)

A measurement device including:

a measurement unit configured to have a light source unit configured to emit measurement light having at least one kind of wavelength for measuring a biological component included inside a living body, a detection unit configured to detect the measurement light emitted from the inside of the living body, and a polarization control unit configured to be provided in at least one position between the light source unit and the living body or between the living body and the detection unit and to control a polarization direction of the measurement light; and an analysis unit configured to compute an optical rotation degree based on a change in a polarization state of the measurement light using a measurement result obtained by the measurement unit and to analyze a concentration of the biological component based on the computed optical rotation degree.

(2)

The measurement device according to (1), wherein the polarization control unit controls the polarization direction of the measurement light so that the measurement light forms two kinds of plane polarized light beams orthogonal to each other.

(3)

The measurement device according to (1) or (2), further including:

a measurement control unit configured to control the measurement unit, wherein the measurement control unit switches polarization directions of the measurement light in a time division manner.

(4)

The measurement device according to any one of (1) to (3), wherein the analysis unit specifies a polarization direction of the measurement light detected using rates of detection intensities of the plane polarized light beams each detected by the detection unit and then computes the optical rotation degree based on a result of the specification.

(5)

The measurement device according to any one of (1) to (4), wherein the polarization control unit controls a polarization direction of the measurement light so that another plane polarized light beam that is different from the two kinds of plane polarized light beams orthogonal to each other is obtained, in addition to the two kinds of plane polarized light beams orthogonal to each other.

(6)

The measurement device according to any one of (1) to (5), wherein the light source unit emits the measurement light having a plurality of kinds of wavelengths different from one another, and wherein the measurement control unit changes a combination of a wavelength of the measurement light and the polarization state at random when selection of a wavelength of the measurement light emitted from the light source unit and control of a polarization direction of the measurement light by the polarization control unit are executed in a time division manner.

(7)

The measurement device according to any one of (1) to (6), wherein the polarization control unit is provided in both positions between the light source unit and the living body and between the living body and the detection unit, and wherein a polarization direction selected by the polarization control unit provided in the position between the living body and the detection unit is set to rotate by a predetermined offset angle with respect to a polarization direction selected by the polarization control unit provided in the position between the light source unit and the living body.

(8)

The measurement device according to any one of (1) to (7), wherein the measurement unit is a measurement section configured to detect the measurement light emitted from the living body as a result of scattering of the measurement light inside the living body and then reflection of the measurement light inside the living body.

(9)

The measurement device according to any one of (1) to (8), wherein the light source unit emits the measurement light having a plurality of kinds of wavelengths different from one another, and wherein the analysis unit acquires a pulse waveform indicating pulsebeats caused by beats of arteries present inside the living body based on a temporal change of the optical rotation degree obtained from a detection result of the measurement light in each of the wavelengths, and then computes a concentration of the biological component in arterial blood using a peak value and a bottom value of the acquired pulse waveform.

(10)

The measurement device according to any one of (1) to (8), wherein the light source unit emits the measurement light having a plurality of kinds of wavelengths different from one another, and wherein the analysis unit computes a concentration of the biological component further using a scattering characteristic spectrum or an absorption spectrum obtained from a detection result of the measurement light in each of the wavelengths.

(11)

The measurement device according to (10), wherein the analysis unit acquires a pulse waveform indicating pulse-beats caused by beats of arteries present inside the living body based on a temporal change of the scattering characteristic spectrum obtained from a detection result of the measurement light in each of the wavelengths, and then computes a concentration of the biological component in arterial blood using a peak value and a bottom value of the acquired pulse waveform.

(12)

The measurement device according to any one of (1) to (11), wherein the analysis unit computes a concentration of glucose in blood.

(13)

The measurement device according to any one of (1) to (12), wherein the analysis unit separates scattered light scattered inside the living body and transmitted light transmitted through the living body based on a polarization plane of the measurement light emitted toward the living body and a polarization plane of the measurement light emitted from the living body.

(14)

The measurement device according to (13), wherein the light source unit emits the measurement light having a plurality of kinds of wavelengths different from one another, and wherein the analysis unit separates the scattered light and the transmitted light based on a polarization plane of the measurement light in each of the wavelengths.

(15)

A measurement method including:

emitting measurement light having at least one kind of wavelength for measuring a biological component included inside a living body;

controlling a polarization direction of the measurement light in at least one position between a light source of the measurement light and the living body or between the living body and a detection unit configured to detect the measurement light emitted from the inside of the living body;

detecting the measurement light emitted from the inside of the living body; and computing an optical rotation degree based on a change in a polarization state of the measurement light using a detection result of the measurement light and analyzing a concentration of the biological component based on the computed optical rotation degree.

(16)

A program causing a computer configured to be capable of communicating with a measuring instrument having a light source unit configured to emit measurement light having at least one kind of wavelength for measuring a biological component included inside a living body, a detection unit configured to detect the measurement light emitted from the inside of the living body, and a polarization control unit configured to be provided in at least one position between the light source unit and the living body or between the living body and the detection unit and to control a polarization direction of the measurement light to execute:

an analysis function of computing an optical rotation degree based on a change in a polarization state of the measurement light using a measurement result obtained by the measuring instrument and analyzing a concentration of the biological component based on the computed optical rotation degree.

(17)

A recording medium having a program recorded therein, the program causing a computer configured to be capable of communicating with a measuring instrument having a light source unit configured to emit measurement light having at least one kind of wavelength for measuring a biological component included inside a living body, a detection unit configured to detect the measurement light emitted from the inside of the living body, and a polarization control unit configured to be provided in at least one position between the light source unit and the living body or between the living body and the detection unit and to control a polarization direction of the measurement light to execute:

an analysis function of computing an optical rotation degree based on a change in a polarization state of the measurement light using a measurement result obtained by the measuring instrument and thereby analyzing a concentration of the biological component based on the computed optical rotation degree.

(18)

A measurement device including:

a measurement unit configured to have a light source unit configured to emit measurement light having at least one kind of wavelength for measuring a biological component included inside a living body, a detection unit configured to detect the measurement light emitted from the inside of the living body, and a polarization control unit configured to be provided in at least one position between the light source unit and the living body or between the living body and the detection unit and to control a polarization direction of the measurement light;

an analysis unit configured to compute an optical rotation degree based on a change in a polarization state of the measurement light using a measurement result obtained by the measurement unit and to analyze a concentration of the biological component based on the computed optical rotation degree; and a measurement control unit configured to control the measurement unit, wherein the measurement unit is a measurement section configured to detect the measurement light emitted from the living body as a result of scattering of the measurement light inside the living body and then reflection of the measurement light inside the living body, and wherein the measurement control unit switches polarization directions of the measurement light in a time division manner.

(19)

A measurement method including:

emitting measurement light having at least one kind of wavelength for measuring a biological component included inside a living body;

controlling a polarization direction of the measurement light in at least one position between a light source of the measurement light and the living body or between the living body and a detection unit configured to detect the measurement light emitted from the inside of the living body;

detecting the measurement light emitted from the inside of the living body; and computing an optical rotation degree based on a change in a polarization state of the measurement light using a detection result of the measurement light and analyzing a concentration of the biological component based on the computed optical rotation degree, wherein the emission and detection of the measurement light are performed by a measurement section configured to detect the measurement light emitted from the living body as a result of scattering of the measurement light inside the living body and then reflection of the measurement light inside the living body, and wherein polarization directions of the measurement light are switched in a time division manner.

(20)

A program causing a computer configured to be capable of communicating with a measuring instrument having a light source unit configured to emit measurement light having at least one kind of wavelength for measuring a biological component included inside a living body, a detection unit configured to detect the measurement light emitted from the inside of the living body, and a polarization control unit configured to be provided in at least one position between the light source unit and the living body or between the living body and the detection unit and to control a polarization direction of the measurement light, the measuring instrument detecting the measurement light emitted from the living body as a result of scattering of the measurement light inside the living body and then reflection of the measurement light inside the living body, to execute:

an analysis function of computing an optical rotation degree based on a change in a polarization state of the measurement light using a measurement result obtained by the measuring instrument and analyzing a concentration of the biological component based on the computed optical rotation degree; and a control function of the measuring instrument.

REFERENCE SIGNS LIST 10 measurement device
101 measurement unit
103 measurement control unit
105 analysis unit
107 storage unit
111 light source unit
113 detection unit
115 polarization control unit (polarization filter)
117 object lens

The invention claimed is:

1. A measurement apparatus for measuring a biological component included inside a living body, said apparatus comprising:

a measurement device having (i) a light source to emit measurement light having a plurality of wavelengths, each wavelength being different from each other, (ii) a detection device to detect the measurement light emitted from the inside of the living body, and (iii) a first polarization control device arrangeable between the light source and the living body and a second polarization control device arrangeable between the living body and the detection device, the first polarization control device and the second polarization control device to control light transmitted therethrough to have polarization directions associated therewith so as to provide a number of polarization states;

a measurement control device to control the measurement device to cause switching in a time division manner of combinations involving the wavelengths of the measurement light emitted from the light source and the polarization directions of the measurement light; and a processing device to compute an optical rotation degree based on a change in a polarization state of the measurement light emitted from the inside of the living body detected by the detection device and to determine a concentration of the biological component based on the computed optical rotation degree, in which each combination of the combinations is different from each other and each said combination represents a wavelength of the measurement light emitted from the light source and a polarization direction of the measurement light, and in which the measurement control device causes the combinations to be switched at random in the time division manner such that a first combination is switched to a second combination which is randomly selected from among the combinations.

2. The measurement apparatus according to claim 1, wherein each of the first polarization control device and the second polarization control device controls the polarization directions of the measurement light to form two plane polarized light beams orthogonal to each other.

3. The measurement apparatus according to claim 1, wherein during operation the detection device detects the measurement light emitted from the living body as a result of scattering of the measurement light inside the living body and then reflection of the measurement light inside the living body.

4. The measurement apparatus according to claim 1, in which during operation the processing device acquires a pulse waveform indicating pulsebeats caused by beats of arteries present inside the living body, and computes a concentration of the biological component in arterial blood using a peak value and a bottom value of the acquired pulse waveform.

5. The measurement apparatus according to claim 1, in which during operation the processing device computes a concentration of the biological component further using a scattering characteristic spectrum or an absorption spectrum obtained from the measurement light in each of the wavelengths.

6. The measurement apparatus according to claim 5, in which during operation the processing device acquires a pulse waveform indicating pulsebeats caused by beats of arteries present inside the living body based on a temporal change of the scattering characteristic spectrum obtained from the measurement light in each of the wavelengths, and computes a concentration of the biological component in arterial blood using a peak value and a bottom value of the acquired pulse waveform.

7. The measurement apparatus according to claim 1, in which during operation the processing device computes a concentration of glucose in blood.

8. The measurement apparatus according to claim 1, in which during operation the processing device separates scattered light scattered inside the living body and transmitted light transmitted through the living body based on a polarization plane of the measurement light emitted toward the living body and a polarization plane of the measurement light emitted from the living body.

9. The measurement apparatus according to claim 8, in which during operation the processing device separates the scattered light and the transmitted light based on a polarization plane of the measurement light in each of the wavelengths.

10. A measurement method for measuring a biological component included inside a living body, said method comprising:
    emitting, by use of a light source, measurement light having a plurality of wavelengths, each wavelength being different from each other;
    detecting, by use of a detecting device, the measurement light emitted from the inside of the living body;
    controlling, by use of a first polarization control device arrangeable between the light source and the living body and a second polarization control device arrangeable between the living body and the detection device, light transmitted therethrough to have polarization directions associated therewith so as to provide a number of polarization states;
    switching, by use of a measurement control device, in a time division manner combinations involving the wavelengths of the measurement light emitted from the light source and the polarization directions of the measurement light; and
    computing, by use of a processing device, an optical rotation degree based on a change in a polarization state of the measurement light emitted from the inside of the living body detected by the detection device and determining a concentration of the biological component based on the computed optical rotation degree,
    in which each combination of the combinations is different from each other and each said combination represents a wavelength of the measurement light emitted from the light source and a polarization direction of the measurement light, and in which the switching of the combinations in the time division manner is performed in a random manner such that a first combination is switched to a second combination which is randomly selected from among the combinations.

11. A non-transitory recording medium having a program recorded therein, the program causing a computer, capable of communicating with a measuring apparatus having a measurement device which includes a light source to emit measurement light having a plurality of wavelengths, each wavelength being different from each other, and a detection device to detect the measurement light emitted from the inside of the living body, upon execution of the program to:
    switch, in a time division manner, combinations involving the wavelengths of the measurement light emitted from the light source and polarization directions of the measurement light; and
    compute an optical rotation degree based on a change in a polarization state of the measurement light emitted from the inside of the living body detected by the detection device and to determine a concentration of the biological component based on the computed optical rotation degree,
    the measurement device having a first polarization control device arrangeable between the light source and the living body and a second polarization control device arrangeable between the living body and the detection device, the first polarization control device and the second polarization control device to control light transmitted therethrough to have polarization directions associated therewith so as to provide a number of polarization states, and
    in which each combination of the combinations is different from each other and each said combination represents a wavelength of the measurement light emitted from the light source and a polarization direction of the measurement light, and in which switching of the combinations in the time division manner is performed in a random manner such that a first combination is switched to a second combination which is randomly selected from among the combinations.

12. The measurement apparatus according to claim 1, in which the polarization directions of the second polarization control device cause light to be rotated by a predetermined offset angle with respect to the polarization directions of the first polarization control device such that the angles associated with the polarization directions of the first polarization control device and the second polarization control device are different.

13. The measurement apparatus according to claim 1, in which the detection device includes a plurality of detectors, each detector of the plurality of detectors has a detectable wavelength band which is different from that of each other detector of the plurality of detectors.

14. The measurement apparatus according to claim 13, in which the plurality of detectors includes a first detector having a first detectable wavelength band and a second detector having a second detectable wavelength band which is different from the first detectable wavelength, and in which the first detectable wavelength band and the second detectable wavelength band partially overlap each other so as to provide a combined detectable wavelength band that is larger than the first detectable wavelength band or the second detectable wavelength band.

* * * * *